US00PP13495P2

(12) United States Plant Patent
Bradford

(10) Patent No.: US PP13,495 P2
(45) Date of Patent: Jan. 21, 2003

(54) NECTARINE TREE NAMED 'SWEET PEARL'

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 0 days.

(21) Appl. No.: 10/014,020

(22) Filed: Dec. 13, 2001

(51) Int. Cl.[7] ..... A01H 5/00
(52) U.S. Cl. ..... Plt./189; Plt./188
(58) Field of Search ..... Plt./189, 188

(56) References Cited

U.S. PATENT DOCUMENTS

PP7,193 P 3/1990 Bradford ..... Plt./190
PP9,960 P 7/1997 Bradford ..... Plt./188

*Primary Examiner*—Bruce R. Campell
*Assistant Examiner*—W C Haas

(57) ABSTRACT

The present invention relates to a nectarine tree, *Prunus persica*, and more particularly to a new distinct variety broadly characterized by a medium size, vigorous, hardy, self-fertile, productive and regular bearing tree. The fruit matures under the ecological conditions described approximately the first week in July, with first picking on Jul. 3, 2001. The fruit is uniformly large in size, very good in flavor, globose in shape, freestone in type, firm in texture, white in flesh color, and red in skin color. The variety was developed as a first generation cross using 'Red Glen'U.S Plant Pat. No. 7,193) yellow flesh nectarine as the selected seed parent and an unnamed white flesh nectarine as the selected pollen parent.

1 Drawing Sheet

CROSS REFERENCE TO RELATED APPLICATIONS

This case is related to co-pending United States Patent application Ser. No. 10/014,021, filed Dec. 13, 2001 drawn to 'SWEET SURPRISE' nectarine.

BOTANICAL CLASSIFICATION

*Prunus persica.*

BACKGROUND OF THE VARIETY

In a continuing effort to improve to quality of shipping fruits, I, the inventor, typically hybridize a large number of peach, nectarine, plum, apricot, and cherry seedlings each year. The present invention relates to a new and distinct variety of nectarine tree, which has been denominated varietally as 'SWEET PEARL'. The present variety was hybridized by me in 1992, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'Red Glen' (U.S. Plant Pat. No. 7,193) yellow flesh nectarine at the selected seed parent and an unnamed white flesh nectarine as the selected pollen parent. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' rootstock (unpatented) upon which the present variety was compatible and true to type.

The present variety is similar to its selected seed parent, 'Red Glen' (U.S. Plant Pat. No. 7,193) nectarine, by producing nectarines that are globose in shape, firm in texture, and almost fully red in skin color, but is distinguished therefrom and an improvement thereon by producing fruit that is white instead of yellow in flesh color, that is subacid instead of acid in flavor, that is freestone instead of clingstone, and that matures about three weeks earlier.

The present variety is most similar to 'Grand Pearl' (U.S. Plant Pat. No. 9,960) nectarine by producing nectarines that are white in flesh color, subacid and sweet in flavor, and mostly red in skin color, but is distinguished therefrom and an improvement thereon by producing fruit that is freestone instead of clingstone and that matures about seven days earlier.

DRAWING

The accompanying photograph exhibits four whole fruits positioned to display the characteristics of the skin color and form, one fruit divided around the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin County), Calif., and was developed at the state of firm ripe on Jul. 9, 2001, on the original tree during its ninth growing season. All major color code designations are by reference to the Inter-Society Color Council, National Buerau of Standards. Common color names are also used occasionally.

Tree

Size: Medium, reaching and maintaining a height of 11' [3.35m. ] after nine growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commerical rootstock for production purposes.

Growth: Spreading and dense.
Form: Vase formed.
Hardiness: Hardy with respect to central California winters.
Heat tolerance: Observed to perform adequately in typical central California climatic conditions, which typically include Prolonged periods of heat.
Drought tolerance: Variety is developed for commercial orchards and Requires regular irrigation.
Production: Very productive, thinning necessary.
Fertility: Self-fertile.
Bearing: Regular bearer with no alternate bearing yet observed.
Trunk:
*Size.*—Medium, reaching a maximum diameter of 5" [127 mm.] after the ninth growing season.
*Texture.*—Rough.
*Bark color.*—Grayish brown [61. gy.Br].
*Lenticels.*—Numerous. Color: Moderate orange yellow [71. m.OY]. Typical Size: ¼" to ⅜" [6.4–9.5 mm.].
Branches:
*Size.*—Diameter of scaffold is 2¼" [57 mm.] measured 12" above the crotch, typical of *Prunus persica*, and dependent upon cultural practices and climatic conditions.
*Texture.*—Smooth on 1st year wood, increasing roughness with age.
*Color.*—1st Year Wood Topside: Grayish red [19. gy.R]. 1st Year Wood Underside: Light yellow green [119. 1.YG]. Older Wood: Dark yellowish brown [78. d.yBr].
*Lenticels.*—Numerous. Color: Deep orange yellow [69. deep OY]. Size: Medium, 1/16" to ⅛" [1.6–3.2 mm.].
Leaves:
*Size.*—Large. Average Length: 6" [152 mm.]. Average width: 1⅝"0 [41 mm.].
*Arrangement.*—Alterate.
*Thickness.*—Medium.
*Form.—Elliptical.*
*Apex.*—Acuminate.
*Base.*—Acute with an average angle of 75 degrees.
*Surface.*—Smooth.
*Color.*—Dorsal Surface: Moderate olive green [125. m.O1G]. Ventral Surface: Moderate yellow green [120. m.YG].
*Margin.*—Finely serrate.
*Venation.*—Pinnately net veined.
*Petiole.*—Average Length: 7/16" [11.1 mm.]. Average Thickness: 1/16" [1.6 mm.]. Color: Brilliant yellow green [116. brill.YG].
*Stipules.*—Number: 2 per leaf, up to 6 per growing tip. Average Length: ¼" [6.4 mm.]. Color: Light yellow green [119. l.YG] when growing.
*Glands.*—Number: 2 to 6. Position: Usually alternate, occasionally opposite, positioned both on the petiole and the base of the leaf blade. Size: Medium. Form: Reniform, but look globose when infant. Color: Brilliant yellow green [116. brill.YG].
*Leaf buds.*—Pointed.
Flower buds:
*Hardiness.*—Hardy, with respect to central California winters.
*Diameter.*—Typically ⅜" [9.5 mm. ]1 week before bloom.
*Length.*—Typically ¾" [19.1 mm. ]1 week before bloom.
*Form.*—Not appressed.
*Surface.*—Pubescent.
*Color.*—Moderate purplish red [258. m.pR].
Flowers: Perfect, complete, perigynous, usually a single pistil, typically thirty or more stamens, five sepals and petal locations alternately positioned.
*Type.*—Showy.
*Average flower diameter.*—1¾" [44.5 mm].
*Number of petals.*—Usually five, with a few double blossoms.
*Petal shape.*—Rounded.
*Petal margin.*—Wavy.
*Average petal diameter.*—⅞" [22.2 mm.].
*Average petal length.*—13/16" [20.6 mm.].
*Petal apex.*—Rounded.
*Petal base.*—Rounded.
*Petal color.*—Light purplish pink [249. l.pPk].
*Anther color.*—Dark red [16. d.R].
*Stigma color.*—Light yellow green [119. l.YG].
*Sepal color.*—Dark purplish red [259. d.pR].
*Sepal length.*—3/16" [5 mm.].
*Sepal width.*—3/16" [5 mm.].
*Average pistil length.*—⅝" [15.9 mm.].
*Average stamen length.*—11/16" [17.5 mm.].
*Fragrance.*—Moderate when nectar is present.
*Blooming period.*—Medium compared with other varieties.
*Onset of bloom.*—One percent on Mar. 1, 2001.
*Date of full bloom.*—Mar. 11, 2001.
*Duration of bloom.*—One to two weeks, dependent on ambient temperature.
*Number per cluster.*—Mostly 1, occasionally 2, rarely more than 2.

FRUIT

Maturity when described: Firm ripe, Jul. 9, 2001.
Date of first picking: Jul. 6, 2001.
Date of last picking: Jul. 20, 2001.
Size: Uniform, large.
*Average diameter axially.*—2⅞" [73.0 mm].
*Average diameter across suture plane.*—2⅞" [73.0 mm.].
*Typical weight.*—7.2 ounces [204 grams].
Form: Uniform, slightly asymmetrical, globose.
*Longitudinal section form.*—Roundish.
*Transverse section through diameter.*—Roundish.
Suture: An inconspicuous line extending from the base to the pistil point becoming a shallow groove near the apex and having a marked depression just beyond the pistil point.
Ventral surface: Rounded, lipped toward the apex.
Lips: Somewhat unequal.
Cavity: Flaring, elongated in the suture plane, suture showing on both sides, Yellowish white [92. yWhite] stem markings typical.
*Depth.*—⅝" [15.9 mm.].
*Breadth.*—1" [25.4 mm.].
Base: Truncate.
Apex: Rounded.
Pistil point: Oblique, negligible in length, depressed within the suture.
Stem: Medium.
*Average length.*—⅜" [9.5 mm.].
*Average width.*—3/19" [4.8 mm.].
Skin:
*Thickness.*—Medium.
*Surface.*—Smooth.
*Tenacity.*—Tenacious to flesh.

*Astringency.*—Nonastringent.
*Tendency to crack.*—Slight.
*Color.*—Very dark red [17. v.d.R] smoothly blending into Moderate red [15.m.R], Yellowish white [92. y.White]. where sun protected, Light yellowish brown [76. 1.yBr] freckling on the cheeks toward the apex.

Flesh:
*Color.*—Greenish white [153. gWhite] from skin to very near the stone, with some Deep red [13. deep R] streaking close to the stone.
*Surface of pit cavity.*—Deep red [13. deep.R] fibers cleanly detaching from the stone.
*Amydalin.*—Scarce.
*Juice.*—Abundant, rich.
*Texture.*—Firm, crisp.
*Fibers.*—Abundant, fine.
*Ripens.*—Earliest at apex along cheeks.
*Flavor.*—Subacid and sweet, ranging from 16 to 18 brix.
*Aroma.*—Moderate to slight.
*Eating quality.*—Best.

STONE

Type: Freestone.
Form: Oval.
Hilum: Narrow.
Base: Straight.
Apex: Acute, with a 3/16" [4.8 mm] tip forming an angle of 40 degress. Sides: Unequal.
Surface: Irregulary furrowed near the apex and pitted toward the base.
Ridges: Jagged toward the base.
Color: Dark grayish reddish brown [47. d.gyrBr].
Average pit wall thickness: 1/4" [6.4 mm.].
Average width: 1" [25.4 mm.].
Average length: 1 5/8" [41.3 mm.].
Tendency to split: None observed.

Kernel:
*Form.*—Oval.
*Pellicle color.*—*Deep yellowish brown* [75. deep yBr].
*Skin color.*—*Pale yellow* [89 .p.Y].
*Vein color.*—Grayish yellowish brown [80 .gy.yBr].
*Taste.*—Sweet.
*Viable.*—Yes.
*Average width.*—7/16" [11.1 mm.].
*Average length.*—3/4" [19.1 mm.].
*Amygdalin.*—Abundant.

USE

Market: Fresh market, long distance shipping, backyard grower.
Keeping quality: Good. Fruit quality observed to remain in good condition in after 21 days in standard cold room at 36° Fahreheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Grand Pearl' (U.S. Plant Pat. No. 9,960) nectarine by producing nectarines that are white in flesh color, subacid and sweet in flavor, and mostly red in skin color, but is distinguished therefrom and an improvement thereon by producing fruit that is freestone instead of clingstone and that matures about seven days earlier.

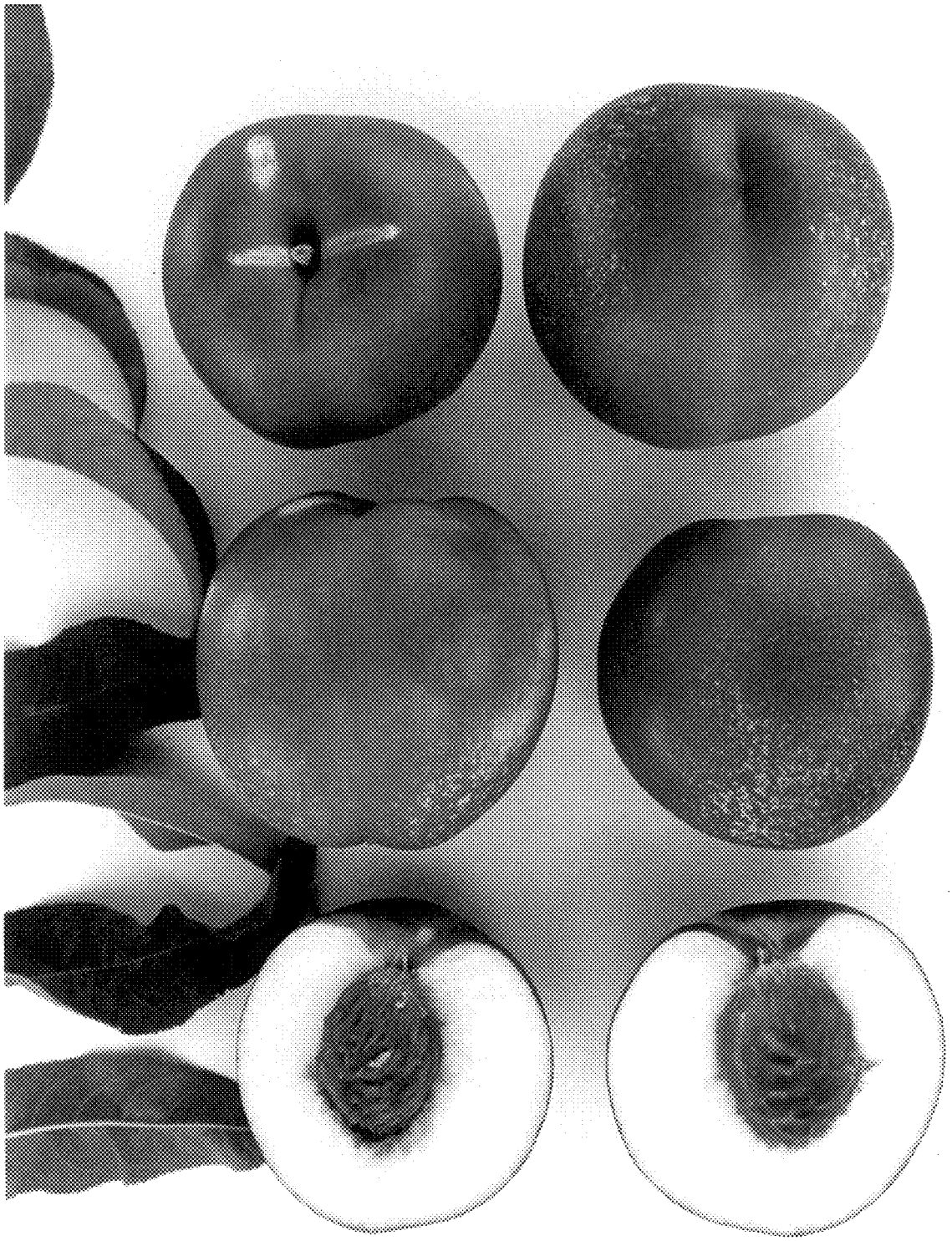

* * * * *